United States Patent [19]

Nakagami et al.

[11] Patent Number: 5,676,927
[45] Date of Patent: Oct. 14, 1997

[54] GRANULAR PREPARATION FOR MRI

[75] Inventors: Hiroaki Nakagami; Manabu Matsumura, both of Tokyo, Japan

[73] Assignee: Daiichi Pharmaceutical Co., Ltd., Tokyo, Japan

[21] Appl. No.: 424,481

[22] PCT Filed: Nov. 12, 1993

[86] PCT No.: PCT/JP93/01658

§ 371 Date: May 12, 1995

§ 102(e) Date: May 12, 1995

[87] PCT Pub. No.: WO94/11033

PCT Pub. Date: May 26, 1994

[30] Foreign Application Priority Data

Nov. 13, 1992 [JP] Japan ................... 4-303500

[51] Int. Cl.$^6$ .................. A61K 49/00; G01N 31/00; G01N 33/48
[52] U.S. Cl. ................ 424/9.32; 424/9.3; 424/9.1
[58] Field of Search ............. 424/9.1, 9.3, 9.31, 424/9.32, 489

[56] References Cited

U.S. PATENT DOCUMENTS

| | | | |
|---|---|---|---|
| 4,719,098 | 1/1988 | Weinmann et al. | 424/9.1 |
| 5,393,525 | 2/1995 | Gundersen | 424/9.32 |

FOREIGN PATENT DOCUMENTS

| | | |
|---|---|---|
| 0409351 | 1/1991 | European Pat. Off. . |
| 0669135 | 8/1995 | European Pat. Off. . |
| 60-16936 | 1/1985 | Japan . |
| WO 91/01148 | 7/1991 | WIPO . |

*Primary Examiner*—John Kight
*Assistant Examiner*—Dameron L. Jones
*Attorney, Agent, or Firm*—Oblon, Spivak, McClelland, Maier & Neustadt, P.C.

[57] ABSTRACT

The present invention relates to a granular preparation for MRI obtained by granulating a viscosity-increasing agent together with a binder and if necessary, a vehicle, a disintegrant, etc., by the use of a fluidized-bed granulation method, and spraying ferromagnetic particles suspended in an aqueous solution of a viscosity-increasing agent or a binder for coating the granules or incorporating the suspension into he granules at the time of granulation to prepare bulky granules. The granular preparation according to the present invention does not undergo coagulation due to gelling at the time of suspending, and can be instantaneously turned into a suspension which is uniform and viscose by mere stirring. Accordingly, the preparation method is simple and easy. Since it is a solid preparation, stability of the ferromagnetic particle is higher than that of an aqueous dispersion, it is free from the problem of putrefaction by microorganisms and molds and is advantageous from the aspects of transportation and storage space.

13 Claims, No Drawings

GRANULAR PREPARATION FOR MRI

DESCRIPTION

1. Technical Field

The present invention relates to contrast agents for MRI (Magnetic Resonance Imaging).

2. Background Art

Clinical applications of MRI have rapidly developed from the beginning of the 1980's, since its first application in the medical field in the early 1970's. MRI is now regarded as an important noninvasive image-forming technique, comparable with X-rays, computed tomography (X-ray CT) and ultrasonic diagnosis. MRI provides images based on nuclear magnetic resonance signals of protons in tissues of living organisms. Since it permits a high freedom in image forming and has high resolution, it was originally considered that contrast agents were not necessary. However, as clinical experience has been accumulated, certain drawbacks and limitations of MRI have come to light, and therefore, various contrast agents for MRI have been developed to provide a clear contrast between the normal tissue and the diseased part.

Contrast agents for MRI are divided into groups of positive contrast agents which intensify signal intensities by shortening the longitudinal relaxation time of protons, and negative contrast agents which weaken signal intensities by shortening the transverse relaxation time of protons. Paramagnetic metal ions belong to the former group, typical examples of which include chelating compounds of gadolinium such as magnebiste.

On the other hand, ferromagnetic particles belong to the latter group. When magnetic particles are administered to a subject orally or per rectum in the MRI diagnosis, artifacts caused by gas or the like in the digestive tract and peristalsis of the digestive tract can be minimized by rendering the digestive tract as a dark image. Therefore, the quality of image diagnosis in the abdominal organs can be enhanced by intensifying the contrast between the digestive tract and the target organ (Japanese patent application laid-open (kokai) SHO 61-501633).

Concerning preparations containing ferromagnetic particles, dispersions prepared by suspending ferromagnetic particles in an aqueous medium containing a viscosity-increasing agent or a surfactant have been proposed for use with administration by oral route or per rectum (Japanese patent application laid-open (kokai) SHO 61-501633).

However, since dispersions are prepared by diluting with water or with an aqueous medium, they easily putrefy due to propagation of microorganisms such as molds and bacteria, and therefore, the addition of preservatives is needed. In order to inhibit the growth of microorganisms such as molds and bacteria, it is required to add preservatives in such amounts that the concentration thereof exceeds a certain threshold value. When contract agents of ferromagnetic preparations are used, relatively large amounts of dose, ranging from 600 to 1,000 ml, must be administered, and therefore, a problem arises in that the total uptake of preservatives can exceed the amount permitted in one day.

In dispersions, most ferromagnetic particles exist as solids suspended therein, and a part of ferromagnetic particles exists in a dissolved state. Generally speaking, a solid state is more stable than a solution state, and therefore, ferromagnetic particles in dispersions are considered disadvantageous compared to those in a solid state with regard to stability.

Moreover, dispersions have the drawback that a large space is required for the storage and transportation of the dispersion preparations. In view of this, granular preparations which are capable of being prepared into a dispersion upon clinical use are desirable compared to preparations supplied, transported and stored in dispersions.

In an attempt to overcome the above drawbacks, granular preparations containing ferromagnetic particles and viscosity-increasing agents have recently been developed (EP 0409351-A1).

However, in order to prepare a dispersion of a granular preparation in water or in an aqueous medium, a stirring operation from 15 seconds to 60 minutes, preferably 2 to 10 minutes, is needed, which is considerably laborious and time-consuming. Accordingly, the disclosed granular preparations are not satisfactory with respect to readiness for use. Moreover, since the granular preparations contain a viscosity-increasing agent, they precipitate and become gelled to form clusters at the bottom of the container, if stirring is insufficient. Once clusters are formed, it is difficult to redisperse this. Furthermore, since such granular preparations which are slow in becoming hydrated provide a dispersion in which swollen particles in a gel state are dispersed in water or in an aqueous medium, they may be difficult to ingest. Therefore, conventional granular preparations are not satisfactory in terms of instant preparation and ease in taking.

Accordingly, an object of the present invention is to provide a contrast agent in a solid form, which is a granular preparation capable of being instantly dispersed to provide a homogeneous and viscous dispersion when suspended in water or in an aqueous medium upon use.

DISCLOSURE OF THE INVENTION

The present invention provides a granular preparation for MRI which comprises bulky particles containing a ferromagnetic material and a viscosity-increasing agent.

Due to the bulkiness of the particles, the granular preparation according to the present invention is not coagulated by gellation when it is prepared into a suspension. It instantly provides a uniform viscous suspension upon stirring. Accordingly, the preparation method is simple and easy. Moreover, since it is a solid preparation, ferromagnetic particles are stably carried therein, and putrefaction by microorganisms and molds is negligible compared with aqueous dispersions. It is also advantageous in handling, in view of the transportation and reduced space for storage.

BEST MODE FOR CARRYING OUT THE INVENTION

The ferromagnetic material which is used in the present invention serves as the active component of the contrast agent for MRI. It encompasses not only ferromagnetic materials, but also ferrimagnetic and superparamagnetic materials. A specific example of the ferromagnetic materials is selected from the group consisting of magnetite ($Fe_3O_4$), gamma-ferric oxide (gamma-$Fe_2O_3$), cobalt ferrite, nickel ferrite, manganese ferrite and mixtures thereof.

In the present invention, the ferromagnetic material may be incorporated by itself. However, it is preferred that the ferromagnetic material first be coated with, embedded in, or carried by a nonmagnetic polymer to provide composite particles, and the resulting particles (hereinafter referred to as ferromagnetic particles) be incorporated into the granular preparation of the invention.

Examples of the above-described nonmagnetic polymer which is used to prepare ferromagnetic particles include naturally-occurred or synthetic polymers such as cellulose, its derivatives and polymer latexes. Of these, sulfonated styrene-divinylbenzene copolymers (for example, WO86/03920) is particularly preferred.

The ferromagnetic particles are prepared by physically combining ferromagnetic crystals with the polymer latex in the surface of the polymer particles for carrying the crystals.

The ferromagnetic particles have an average diameter of not more than 50 µm and preferably 0.1 to 20 µm.

The amount of the ferromagnetic material or ferromagnetic particles contained in the granular preparation of the present invention is suitably determined with reference to the expected efficacy of the preparation, and generally, from about 1 to 10% by weight (hereinafter referred to simply as %) based on the total weight of the preparation.

The granular preparation of the present invention is characterized by comprising a viscosity-increasing agent.

The viscosity-increasing agent which is used in the granular preparation of the present invention is soluble in water or swells in the presence of water. Moreover, the viscosity-increasing agent must be difficult to decompose in a living body and must be physiologically acceptable when administered to a living body.

When such a viscosity-increasing agent is used, the inner walls of the digestive tract are covered by ferromagnetic particles, which render the digestive tract as a dark image, thereby intensifying the contrast between the digestive tract and the target organs.

Examples of the viscosity-increasing agent include cellulose derivatives, magnesium aluminum silicate (Veegum), xanthan gum, and the like. Specific examples of the cellulose derivatives which are useful as the viscosity-increasing agent include methylcellulose, carboxymethylcellulose-Na, crystalline cellulose.carboxymethylcellulose-Na, and the like. They may be used singly or in combination of two or more.

The viscosity-increasing agent according to the present invention is generally incorporated in an amount of 3 to 90%, particularly 15 to 80%, based on the total weight of the preparation.

Furthermore, the granular preparation of the present invention may contain disintegrants, binders, vehicles and the like in addition to the viscosity-increasing agent.

Examples of the disintegrants include corn starch, carmellose calcium, hydroxypropylcellulose of low substitution degree and cross carmellose sodium. They may be incorporated in amounts of not more than 20%. Generally speaking, it is preferred that they be incorporated in amounts from 2 to 10% based on the total weight of the preparation.

Examples of the binders include the above-mentioned viscosity-increasing agents, hydroxypropylcellulose, hydroxypropylmethylcellulose, polyvinyl pyrrolidone, polyvinyl alcohol, and the like. The amounts of the binders are generally 10% or less, and preferably from 2 to 8%, based on the total weight of the preparation.

Examples of the vehicles include corn starch, partly pregelatinized starch, lactose and mannitol. The amounts of the vehicles are not particularly limited. Preferably, they are incorporated in a range from 1 to 95%.

When a surfactant is incorporated into the granular preparation of the present invention, the suspension property is improved and a homogeneous dispersion is obtained. Examples of the surfactant which will facilitate dispersing of particles include those which are generally employed in the art, such as polysorbate 80, polyoxyethylene, polyoxypropylene copolymers, and the like (Japanese patent application laid-open (kokai) SHO 61-501633). They are incorporated in amounts from 0.01 to 15% based on the total weight of the preparation.

Examples of additives other than those mentioned above include antioxidants, sweeteners, flavors, colorants, and the like. Specific examples of the antioxidants include sodium sulfite, sodium hydrogensulfite, sodium hydrogenthiosulfate, ascorbic acid, thioglycerol, tocopherol, dibutylhydroxytoluene and butylhydroxyanisole. Moreover, the granular preparation may optionally contain suitable sweeteners, flavors, colorants and the like.

It is necessary that the granular preparation according to the present invention take the form of bulky particles. The term "bulky particles" means that the particles have a small apparent density. The apparent density is preferably not more than 0.4 g/ml, and more preferably from 0.1 to 0.4 g/ml.

Generally, the particle diameter of the granular preparation of the present invention is preferably in the range of 150 to 1400 µm. Particularly, it is preferred that particles having a diameter of not more than 150 µm exist in a proportion of not more than 20% of the total particles.

The viscosity of an aqueous suspension of the granular preparation of the present invention is preferably from 50 to 2000 cp after being completely hydrated.

The granular preparation of the present invention is obtained by a granulation method.

Granulation is an operation of converting a starting material in the form of powder, block, or solution into particles. Methods of granulation for preparing medicines are generally divided into dry-granulation methods and wet-granulation methods from the aspects of mechanism of apparatus and granulating mechanism of starting powders. The dry-granulation methods comprise a compression granulation method and a melting granulation method.

Among the wet-granulation methods, four methods are widely used: an extrusion granulation method using a cylindrical granulation machine, marumerizer, pelleter, and the like; a crushing granulation method using a speed mill or the like to crush a wet mixture; another crushing granulation method using a minimizer, power kneader, speed mill, or the like; a tumbling granulation method making use of a phenomenon which occurs during rotation; and a fluidized-bed granulation method such as a spray-drying (the Japanese Pharmacopoeia A-73 to 74). Of these methods, the fluidized-bed granulation method is preferable for obtaining the bulky granular preparation of the present invention.

According to the fluidized-bed granulating method, powders are kept in a fluid state, to which a solution containing a binder is sprayed for cohering and granulating the particles. In more detail, a binder is sprayed onto a layer of floating powders from a nozzle attached to the granulating apparatus for inducing cohesion of particles to allow them to grow into homogeneous particles.

By contrast, according to the tumbling method, powder is wetted, a binder is added thereto if necessary, and subsequently vibration or rotation movement is applied to make spherical particles due to cohesion. Granular preparations obtained by a method which produces granules having a high apparent density, like this method, precipitate when they are added in water or in an aqueous medium. Such preparations require a stirring time of at least 30 seconds and preferably 1 minute or more for making a dispersion without causing coagulation, and therefore, a very short stirring of 5 seconds or so as achieved in the present invention cannot provide a suspension. This is because granular preparations having a high apparent density have less voids compared to those having a low apparent density, and therefore, water or an aqueous medium permeates into the granules slowly, causing slow hydration and dissolution of viscosity-increasing agents to further slow down the speed of increase of the viscosity. Accordingly, if stirring is insufficient, granules precipitate, form a gel at the bottom of the container, and produce clusters which will no more be dispersed again.

By extrusion granulation, crushing granulation or by tumbling granulation, particles undergo relatively strong shear stress or compression stress during the granulation step, which results in unpreferable granules having a high apparent density.

The granular preparation of the present invention which can instantly provide a dispersion is preferably prepared by the combination of fluidized-bed granulation and spray coating. More specifically, a ferromagnetic material or ferromagnetic particles, which may be added at the time of granulation, are preferably dispersed in an aqueous solution of a viscosity-increasing agent or a binder, and the resulting dispersion may be sprayed for coating onto nuclei particles of additives other than ferromagnetic particles obtained by fluidized-bed granulation in advance.

The thus-obtained granules have a low apparent density, do not precipitate when added in water or in an aqueous medium, are instantly and readily dispersed only by a stirring of 5 seconds or so without forming clusters or coagulation, and provide a viscous homogeneous suspension with ease. Since granular preparations having a low apparent density have a lot of voids compared to granular preparations having a high apparent density, water or an aqueous medium can easily permeate into the granular preparations. Accordingly, the viscosity-increasing agents contained therein can easily be hydrated or dissolved to quickly elevate the viscosity of the system, achieving an instant dispersion by a stirring of 5 seconds or so without causing precipitation. Furthermore, the granular preparations having a low apparent density according to the invention have a lot of voids, and therefore, clusters are hardly formed even though gelation occurs during dispersion.

EXAMPLES

The present invention will next be described more specifically by way of examples, comparative examples, and test example, which should not be construed as limiting the invention.

Using various viscosity-increasing agents, binders, vehicles and disintegrants, the below described 9 preparations were prepared. The formulations are shown in Table 1.

Comparative Example 1

15 g of polyvinylpyrrolidone (hereinafter referred to as PVP) was dissolved in water in advance, and 3.0 g of ferromagnetic particles* were suspended therein. Water was added to make a total volume of 100 ml, and thus a PVP binding solution containing ferromagnetic particles was obtained. 48.0 g of xanthan gum, 84 g of lactose and 150 g of corn starch were placed in a tumbling granulator, then the PVP binding solution containing ferromagnetic particles was added thereto for granulation. The granules obtained were screened by the use of a sieve No. 12, and those which did not pass the sieve were crushed and screened again by the use of a sieve No. 12, and combined with the previously obtained through-sieve granules. Screening of granules was performed again using a sieve No. 42. Granules which passed through the No. 42 sieve were removed to obtain a granular preparation. *: The ferromagnetic particles used in this example were prepared by suspending solid ferromagnetic particles in water with a proportion of 12 to 14% (hereinafter the same applies).

Comparative Example 2

2.5 g of hydroxypropylmethylcellulose (hereinafter referred to as HPMC) was dissolved in water in advance, and water was added thereto for making a total volume of 83 ml to prepare an HPMC solution. 37.5 g of carboxymethylcellulose-Na (hereinafter referred to as CMC-Na), 37.5 g of veegum, 100 g of lactose and 65 g of corn starch were placed in a tumbling granulator, then the HPMC binding solution was added thereto for granulation. The granules obtained were screened by the use of a sieve No. 12, and granules which remained on the sieve were crushed and screened again by the use of a sieve No. 12 for combining with the previously obtained through-sieve granules. Screening of granules was performed again using a sieve No. 42. Granules which passed through the No. 42 sieve were removed to obtain crude granules.

2.4 g of ferromagnetic particles was suspended in an aqueous solution of 1.2 g of HPMC dissolved in water in advance, and 50 ml in total of a ferromagnetic particle-containing coating solution was prepared. 116.4 g of the core granules were placed in a fluidized-bed granulator, and the ferromagnetic particle-containing coating solution was sprayed thereto. Subsequently, granules were screened by the use of a No. 12 sieve, and granules which did not pass through the sieve were removed to prepare a granular preparation containing ferromagnetic particles.

Comparative Example 3

2.5 g of HPMC was dissolved in water in advance, and water was added thereto for making a total volume of 83 ml to prepare an HPMC binding solution. 75 g of methylcellulose (hereinafter referred to as MC), 100 g of lactose and 68.8 g of corn starch were placed in a tumbling granulator, then the HPMC binding solution was added thereto for granulation. The granules obtained were screened by the use of a sieve No. 30, and granules which did not pass the sieve were crushed and screened again by the use of a sieve No. 30 for combining with the previously obtained through-sieve granules. Screening of granules was performed again using a sieve No. 100. Granules which passed through the No. 100 sieve were removed to obtain core granules.

1.2 g of ferromagnetic particles was suspended in an aqueous solution containing 0.6 g of HPMC which had been dissolved in water in advance, thereby 25 ml in total of a ferromagnetic particle-containing coating solution was prepared. 118.2 g of the core granules were placed in a fluidized-bed granulator, and the ferromagnetic particle-containing coating solution was sprayed thereto. Thereafter, granules were screened by the use of a No. 20 sieve, and granules which remained on the sieve were removed to prepare a granular preparation containing ferromagnetic particles.

Example 1

12.0 g of HPMC was dissolved in water in advance, and water was added thereto to prepare an HPMC binding solution having a total volume of 200 ml. 40.0 g of CMC-Na, 126 g of lactose, 16.0 g of hydroxypropylcellulose having a low substitution degree were placed in a fluidized-bed granulator, then the HPMC binding solution was sprayed thereto for granulation. The granules obtained were screened by the use of a sieve No. 12, and granules which remained on the sieve were crushed in mortar and screened again by the use of a sieve No. 12 for combining with the previously obtained through-sieve granules to obtain core granules.

2.4 g of ferromagnetic particles was suspended in an aqueous solution containing 1.2 g of HPMC which had been dissolved in water in advance, and 50 ml in total of a ferromagnetic particle-containing coating solution was prepared. 116.4 g of the core granules were placed in a fluidized-bed granulator, and the ferromagnetic particle-containing coating solution was sprayed thereto. Subsequently, granules were screened by the use of a No. 12 sieve, and granules which did not pass through the sieve were removed to prepare a granular preparation containing ferromagnetic particles.

Example 2

9.0 g of hydroxypropylcellulose (hereinafter referred to as HPC) was dissolved in water in advance, in which 3.0 g of ferromagnetic particles were suspended. Water was added thereto for making a total volume of 300 ml to prepare a HPC binding solution containing ferromagnetic particles. 30.0 g of xanthan gum, 90 g of crystalline cellulose.carboxymethylcellulose-Na (hereinafter referred to as Avicel RC-591), 18 g of lactose were placed in a fluidized-bed granulator, and then the HPC binding solution containing ferromagnetic particles was sprayed thereto for granulation. The granules obtained were screened by the use of a sieve No. 12, and granules which did not pass the sieve were crushed in mortar and screened again by the use of a sieve No. 12 for combining with the previously obtained through-sieve granules to obtaining a granular preparation containing ferromagnetic particles.

Example 3

10.0 g of HPC was dissolved in water in advance, water was added thereto to make a total volume of 200 ml to prepare a HPC binding solution containing HPC. 80.0 g of MC, 80.0 g of Avicel RC-591 and 18.0 g of corn starch were placed in a fluidized-bed granulator, then the HPC binding solution was sprayed thereto for granulation. The granules obtained were screened by the use of a sieve No. 12, and granules which did not pass the sieve were crushed in mortar and screened again by the use of a sieve No. 12 for combining with the previously obtained through-sieve granules to obtain core granules.

4.0 g of ferromagnetic particles was suspended in an aqueous solution of 2.0 g of HPC which had been dissolved in water in advance, and 80 ml in total of a ferromagnetic particle-containing coating solution was prepared. 94.0 g of the core granules was placed in a fluidized-bed granulator, and the ferromagnetic particle-containing coating solution was sprayed thereto. Thereafter, granules were screened by the use of a No. 12 sieve, and granules which did not pass through the sieve were removed to prepare a granular preparation containing ferromagnetic particles.

Comparative Example 4

1.0 g of ferromagnetic particles, 10.0 g of CMC-Na, 20.0 g of lactose, 17.0 g of corn starch and 2.0 g of HPMC were homogeneously mixed in a mortar.

Comparative Example 5

3.0 g of HPMC was dissolved in water in advance, and water was added thereto to make a total volume of 100 ml to prepare a HPMC binding solution. 189 g of lactose and 108.0 g of corn starch were placed in a tumbling granulator, and then the HPMC binding solution was added thereto for granulation. The granules obtained were screened by the use of a sieve No. 12, and granules which did not pass the sieve were crushed in mortar and screened again by the use of a sieve No. 12 for combining with the previously obtained through-sieve granules. Screening of granules was performed again using a sieve No. 42. Granules which passed through the No. 42 sieve were removed to obtain core granules.

2.4 g of ferromagnetic particles was suspended in an aqueous solution of 1.2 g of HPMC which had been dissolved in water in advance, and 50 ml in total of a ferromagnetic particle-containing coating solution was prepared. 116.4 g of the core granules was placed in a fluidized-bed granulator, and the ferromagnetic particle-containing coating solution was sprayed thereto. Thereafter, granules were screened by the use of a No. 12 sieve, and granules which did not pass through the sieve were removed to prepare a granular preparation containing ferromagnetic particles.

Comparative Example 6

6.0 g of HPMC was dissolved in water in advance, to which 3.0 g of ferromagnetic particles were suspended. Water was added thereto to make a total volume of 200 ml to prepare a HPMC binding solution containing ferromagnetic particles. 90.0 g of lactose and 51.0 g of corn starch were placed in a fluidized-bed granulator, then the HPMC binding solution containing ferromagnetic particles was sprayed for granulation. The granules obtained were screened by the use of a sieve No. 12, and granules which did not pass the sieve were crushed in mortar and screened again by the use of a sieve No. 12 for combining with the previously obtained through-sieve granules to obtain a granular preparation containing ferromagnetic particles.

TABLE 1

| | Amounts of components in Examples and Reference Examples | | | | | | | | |
|---|---|---|---|---|---|---|---|---|---|
| | 1 | 2 | 3 | 4 | 5 | 6 | 7 | 8 | 9 |
| Granulation method | Tumble | Tumble | Tumble | Fluid | Fluid | Fluid | Mortar | Tumble | Fluid |
| Examples (Comparative Examples) | Comp. Ex. 1 | Comp. Ex. 2 | Comp. Ex. 3 | Ex. 1 | Ex. 2 | Ex. 3 | Comp. Ex. 4 | Comp. Ex. 5 | Comp. Ex.6 |
| Timing of adding ferromagnetic particles | During granulation | During coating | During coating | During coating | During granulation | During coating | During mortar | During coating | During granulation |
| | Amounts of components (upper row: mg, lower row: %) | | | | | | | | |

TABLE 1-continued

Amounts of components in Examples and Reference Examples

| Granulation method<br>Examples<br>(Comparative Examples) | | 1<br>Tumble<br>Comp.<br>Ex. 1 | 2<br>Tumble<br>Comp.<br>Ex. 2 | 3<br>Tumble<br>Comp.<br>Ex. 3 | 4<br>Fluid<br>Ex. 1 | 5<br>Fluid<br>Ex. 2 | 6<br>Fluid<br>Ex. 3 | 7<br>Mortar<br>Comp.<br>Ex. 4 | 8<br>Tumble<br>Comp.<br>Ex. 5 | 9<br>Fluid<br>Comp.<br>Ex. 6 |
|---|---|---|---|---|---|---|---|---|---|---|
| Ferromagnetic<br>particles | | 100<br>1 | 100<br>2 | 100<br>1 | 100<br>2 | 100<br>2 | 100<br>4 | 100<br>2 | 100<br>2 | 100<br>2 |
| Thickener | Xanthan<br>gum | 1600<br>16 | | | | 1000<br>20 | | 1000<br>20 | | |
| | CMC(Na) | | 750<br>15 | | 1000<br>20 | | | | | |
| | Methyl-<br>cellulose | | | | | | 1000<br>40 | | | |
| | Crystalline<br>cellulose<br>CMCNa | | | 3000<br>30 | | 3000<br>60 | 1000<br>40 | | | |
| | Veegum | | 750<br>15 | | | | | | | |
| Binder | HPC | | | | | 300<br>6 | 175<br>7 | | | |
| | HPMC | | 100<br>2 | 150<br>1.5 | 350<br>7 | | | 200<br>4 | 100<br>2 | 200 |
| | PVP | 500<br>5 | | | | | | | | |
| Vehicle | Lactose | 2800<br>28 | 2000<br>40 | 4000<br>40 | 3150<br>63 | 600<br>12 | | 2000<br>40 | 3000<br>60 | 3000<br>60 |
| | Corn starch | 5000<br>50 | 1300<br>26 | 2750<br>27.5 | | | 225<br>9 | 1700<br>34 | 1800<br>38 | 1700<br>34 |
| Disinte-<br>grant | HPC of low<br>substitution<br>degree | | | | 400<br>8 | | | | | |
| Total (mg) | | 10000 | 5000 | 10000 | 5000 | 5000 | 2500 | 5000 | 5000 | 5000 |

CMC(Na); carboxymethylcellulose (sodium): HPC; hydroxypropylcellulose: HPMC; hydroxypropylmethylcellulose: PVP; polyvinylpyrrolidone: Tumble; tumbling granulation method: Fluid; fluidized-bed granulation method: Mortar; mortar mixing method: During mortar; during mortar mixing Test Example 1

(Measurement of particle size distribution)

20 g each of the granular preparations or mortar mixtures prepared in Examples 1–3 and Comparative Examples 1–6 was classified using a 12 mesh sieve and a 100 mesh sieve set on a sieve shaker (Ro-tap shaker, trademark) for 5 minutes. Based on the proportion by weight of the classified particles, a particle size distribution was obtained. The particle size distribution of the granules obtained in Examples 1–3 and Comparative Examples 1–3; 5–6 was such that granules having a diameter of 150 to 1400 μm were present in a proportion of not less than 90% (Table 2). By contrast, the particle size distribution of the mixture obtained in Comparative Example 4, which were prepared by mixing ferromagnetic particles and additives in mortar was such that powders having a diameter of less than 150 μm were present in a proportion of not less than 99%.

TABLE 2

Distribution of particle size

| Diam-<br>eter<br>of | Distribution of particle size (%) | | | | | | | | |
|---|---|---|---|---|---|---|---|---|---|
| parti-<br>cles | Comparative<br>Examples | | | Examples | | | Comparative<br>Examples | | |
| μm | 1 | 2 | 3 | 1 | 2 | 3 | 4 | 5 | 6 |
| 1400– | 100 | 100 | 99.6 | 97.4 | 97 | 93.2 | 0.7 | 99.3 | 98.6 |

TABLE 2-continued

Distribution of particle size

| Diam-<br>eter<br>of | Distribution of particle size (%) | | | | | | | | |
|---|---|---|---|---|---|---|---|---|---|
| parti-<br>cles | Comparative<br>Examples | | | Examples | | | Comparative<br>Examples | | |
| μm | 1 | 2 | 3 | 1 | 2 | 3 | 4 | 5 | 6 |
| 150<br>150 or<br>less | 0 | 0 | 0.4 | 2.6 | 3 | 6.8 | 99.3 | 0.7 | 1.4 |

Note: 1400 μm corresponds to Mesh No. 12, and 150 μm corresponds to Mesh No. 100.

Test Example 2

(Measurement of the apparent density)

15 g each of granular preparations obtained in Examples 1–3 and Comparative Examples 1, 2, 3, 5 and 6 and a mortar mixture obtained in Comparative Example 4 was taken and placed in a 100 ml messcylinder, respectively, and then the messcylinder was attached to a tapping machine. After tapping 200 times, the surface of the sample in the messcylinder was made flat by the use of a spatula, and the volume of the sample was visually read. The apparent density was calculated according to the following equation:

Apparent density=(Quantity of sample (15 g))/(Apparent volume (ml))

The apparent densities of the particles of the granular preparations prepared in Examples 1–3 and Comparative Example 6, which were prepared by a fluidized-bed granulation method were all not more than 0.4 g/ml. By contrast, the apparent densities of the particles of the granular preparations prepared in Comparative Examples 1, 2, 3 and Comparative Example 5, which were prepared by a tumbling granulation method were all not less than 0.5 g/ml. The apparent density of the mortar mixture obtained in Comparative Example 4 which was not granulated was 0.77 g/ml.

Test Example 3

(Measurement of viscosity)

A granular preparation in an amount equivalent to 100 mg of ferromagnetic particles was dispersed in 200 ml of water. After allowing it to stand overnight, the dispersion which presented a homogeneous suspension was subjected to viscosity measurement using a B-type viscometer in a temperature range of 18° to 22° C. at 60 rpm. Spindle No. 3 was used for measuring the viscosity of the suspensions prepared with Examples 1–3 granular preparations and Comparative Examples 1–4 granular preparations, and spindle No.1 was used for measuring the viscosity of the suspensions prepared with Comparative Examples 5 and 6 preparations. Those which were granulated together with viscosity-increasing agents, namely those using Examples 1–3 and Comparative Examples 1–3 preparations exhibited 200 to 2000 cp (centipoises). Use of Comparative Example 4 preparation also exhibited a similar value (Table 3). Use of preparations of Comparative Examples 5 and 6 which did not contain a viscosity-increasing agent exhibited not more than 5 cp.

TABLE 3

| Comparison of apparent density and viscosity | | | | | | | | | |
|---|---|---|---|---|---|---|---|---|---|
| | Comparative Examples | | | Examples | | | Comparative Examples | | |
| | 1 | 2 | 3 | 1 | 2 | 3 | 4 | 5 | 6 |
| Apparent density (g/ml) | 0.77 | 0.71 | 0.50 | 0.26 | 0.30 | 0.16 | 0.77 | 0.53 | 0.34 |
| Viscosity (cp) | 558 | 266 | 1960 | 278 | 964 | 280 | 262 | 4.2 | 1.5 |

Test Example 4

(Aggregation of particles during preparation of a solution to be administered)

A granular preparation in an amount equivalent to 100 mg of ferromagnetic particles was added to 100 ml of water, followed by immediate stirring with a spatula for 1 minute. The presence or absence of aggregation of particles was visually observed. When the preparations of Examples 1–3 and Comparative Examples 1–3 were used, no aggregation was observed during preparation of a solution (Table 4).

Aggregation of particles was observed when a Comparative Example 4 preparation which contained a viscosity-increasing agent but was not granulated was used. Moreover, no aggregation was observed when the granular preparations of Comparative Examples 5 and 6 which did not contain a viscosity-increasing agent were used.

TABLE 4

| Aggregation of particles during preparation of a solution to be administered | | | | | | | | | |
|---|---|---|---|---|---|---|---|---|---|
| | Comparative Examples | | | Examples | | | Comparative Examples | | |
| | 1 | 2 | 3 | 1 | 2 | 3 | 4 | 5 | 6 |
| Aggregation of particles | None | None | None | None | None | None | Observed | None | None |

Test Example 5

(Time required for preparing a suspension to be administered in which precipitation is not observed)

A granular preparation in an amount equivalent to 100 mg of ferromagnetic particles was added to 200 ml of water, followed by immediate stirring with a spatula for 5 seconds for dispersion. Precipitation of particles was observed for 1 minute. When precipitation was observed, a granular preparation in an amount equivalent to 100 mg of ferromagnetic particles was separately added to 200 ml of water, and stirred for a prolonged period of time until precipitation is no more observed. The stirring time which was required for observing no precipitation was taken as "time A", which was counted for the period of time required for preparing a solution to be administered. Among the preparations of Examples 1–3 and Comparative Examples 1–3, which were granulated together with a viscosity-increasing agent, the time A for preparations of Comparative Examples 1–3 obtained by a tumbling granulation method was 70 to 90 seconds, whereas time A for preparations of Examples 1–3 obtained by a fluidized-bed granulation method was short and 5 seconds (Table 5). The preparation of Comparative Example 4 which contained a viscosity-increasing agent but was not granulated formed aggregation of particles at the time of preparing a solution to be administered and therefore, measurement was not possible.

Test Example 6

(Time required for suspending)

A granular preparation in an amount equivalent to 20 mg of ferromagnetic particles was taken and dispersed in 40 ml of water. The resulting dispersion was shaken with a shaking apparatus. The period of time during which particles are uniformly suspended and can no more be visually observed was defined as the time required for suspending. In Examples 1 to 3 where granules containing a viscosity-increasing agent were prepared by a fluidized-bed method, the resulting granules exhibited shorter the time required for suspending (measured by shaking time with a shaking apparatus), compared to those obtained in Comparative Examples 1 to 3 which employed a tumbling granulation method (Table 5).

TABLE 5

| | Comparison of preparation time | | | | | | | | |
|---|---|---|---|---|---|---|---|---|---|
| | Comparative Examples | | | Examples | | | Comparative Examples | | |
| | 1 | 2 | 3 | 1 | 2 | 3 | 4 | 5 | 6 |
| Time A | Time (seconds) | | | | | | | | |
| | 70 | 80 | 90 | 5 | 5 | 5 | * | 640 | 10 |
| Time B | | | | Time (minutes) | | | | | |
| | 11 | 12 | 8 | 4 | 4 | 7 | 20 | 10 | 1 |

Time A: Period of time (seconds) of stirring required until precipitation of particles is no more observed.
Time B: Period of time (minutes) required for preparing a homogeneous suspension.
*Measurement could not be carried out due to aggregation. Preparations of Comparative Examples 1, 2 and 3 were prepared by tumbling granulation method, and Preparations of Examples 1, 2 and 3 were prepared by fluidized-bed granulation method.

Test Example 7

(Suspension Stability)

A granular preparation in an amount equivalent to 100 mg of ferromagnetic particles was taken and dispersed in 200 ml of water. After allowing it to stand overnight, a homogeneous suspension was stirred with a spatula. The state of suspension was observed after 30 minutes and 24 hours. The suspensions using preparations of Examples 1–3 and Comparative Examples 1–4 which contained a viscosity-increasing agent exhibited an excellent suspension stability. By contrast, the suspensions using preparations of Comparative Examples 5 and 6 which did not contain a viscosity-increasing agent were both separated in 30 minutes (Table 6).

TABLE 6

| | Suspension stability of suspensions | | | | | | | | |
|---|---|---|---|---|---|---|---|---|---|
| | Comparative Examples | | | Examples | | | Comparative Examples | | |
| | 1 | 2 | 3 | 1 | 2 | 3 | 4 | 5 | 6 |
| After 30 minutes | Good | Good | Good | Good | Good | Good | Good | Separated | Separated |
| After 24 hours | Good | Good | Good | Good | Good | Good | Good | Separated | Separated |

Good; Stable, and homogeneous suspension was maintained.
Separated: Poor stability, and precipitation was observed.

Industrial Applicability

The granular preparation of the present invention provides a stable, viscous, and uniform dispersion which does not cause precipitation of particles by a mere stirring/suspending of the preparation in water or in an aqueous medium. The granular preparation of the invention does not form clusters at the time of suspending. In addition, it provides a suspension which is suitable for administering to human subjects and which can be instantly prepared.

Since the present preparation is in a solid form, it is free from putrefaction due to microorganisms and molds compared with aqueous dispersions, and is advantageous in handling from the aspects of transportation and storage space.

Accordingly, the granular preparation of the present invention is very useful as an negative contrast agent for MRI which is dosed orally or per rectum and prepared into a suspension upon use.

We claim:

1. A granular preparation for magnetic resonance imaging, comprising bulky granules which contain a ferromagnetic material and a viscosity-increasing agent, wherein the apparent density of the granules is not more than 0.4 g/ml.

2. The granular preparation according to claim 1, which immediately disperses in water or in an aqueous medium when mixed therewith to provide a uniform viscous aqueous suspension.

3. The granular preparation according to claim 1, which is prepared by a fluidized-bed granulation method or by a combination of a fluidized-bed granulation method and a spray-coating method.

4. The granular preparation according to claim 1, wherein the ferromagnetic material exhibits ferromagnetism, ferrimagnetism or superparamagnetism.

5. The granular preparation according to claim 1, wherein the ferromagnetic material is in the form of a particle which is coated by, embedded into or carried by a non-magnetic polymer.

6. The granular preparation according to claim 1, wherein the ferromagnetic material is selected from the group consisting of magnetite ($Fe_3O_4$), gamma-ferric oxide (gamma-$Fe_2O_3$), cobalt ferrite, nickel ferrite, manganese ferrite and mixtures thereof.

7. The granular preparation of claim 5, wherein said ferromagnetic particles have an average diameter of 0.1 to 20 μm.

8. The granular preparation of claim 1, comprising 1–10% by weight of said ferromagnetic material, based on the total weight of the preparation.

9. The granular preparation of claim 1, comprising 15–80% by weight of said viscosity-increasing agent, based on the total weight of the preparation.

10. The granular preparation of claim 1, further comprising at least one member selected from the group, consisting of disintegrants, binders, vehicles and surfactants.

11. The granular preparation of claim 1, wherein the apparent density of the granules is 0.1–0.4 g/ml.

12. The granular preparation of claim 1, wherein said granules have a particle diameter of 150–1,400 μm.

13. The granular preparation of claim 12, wherein said granules having a diameter of not more than 150 μm exist in a proportion of not more than 20% of the total particles.

* * * * *

UNITED STATES PATENT AND TRADEMARK OFFICE
CERTIFICATE OF CORRECTION

PATENT NO. : 5,676,927
DATED : OCTOBER 14, 1997
INVENTOR(S) : Hiroaki NAKAGAMI, et al It is certified that error appears in the above-identified patent and that said Letters Patent is hereby corrected as shown below:

Column 11, line 55, "100 ml" should read --200 ml--.

Signed and Sealed this

Twenty-second Day of June, 1999

Attest:

Q. TODD DICKINSON

*Attesting Officer*    *Acting Commissioner of Patents and Trademarks*